(12) United States Patent
Scott et al.

(10) Patent No.: US 8,277,396 B2
(45) Date of Patent: Oct. 2, 2012

(54) METHOD AND APPARATUS FOR ASSESSING PROPRIOCEPTIVE FUNCTION

(75) Inventors: Stephen H. Scott, Kingston (CA); Ian E. Brown, Kingston (CA)

(73) Assignee: Queen's University at Kingston, Kingston, ON (CA)

( * ) Notice: Subject to any disclaimer, the term of this patent is extended or adjusted under 35 U.S.C. 154(b) by 0 days.

(21) Appl. No.: 11/979,467

(22) Filed: Nov. 2, 2007

(65) Prior Publication Data

US 2008/0108883 A1    May 8, 2008

Related U.S. Application Data

(60) Provisional application No. 60/856,015, filed on Nov. 2, 2006.

(51) Int. Cl.
*A61B 5/103* (2006.01)
(52) U.S. Cl. ............................................. 600/595; 414/5
(58) Field of Classification Search .................. 600/595; 414/5
See application file for complete search history.

(56) References Cited

U.S. PATENT DOCUMENTS

| | | | |
|---|---|---|---|
| 5,466,213 A | 11/1995 | Hogan | |
| 5,476,441 A | 12/1995 | Durfee | |
| 5,961,541 A | 10/1999 | Ferrati | |
| 6,155,993 A * | 12/2000 | Scott | 600/595 |
| 6,609,017 B1 * | 8/2003 | Shenoy et al. | 600/372 |
| 6,692,449 B1 * | 2/2004 | Brown | 600/595 |
| 7,066,896 B1 * | 6/2006 | Kiselik | 601/5 |
| 2003/0115954 A1 | 6/2003 | Zemlyakov | |
| 2006/0022833 A1 | 2/2006 | Ferguson | |
| 2006/0293617 A1 * | 12/2006 | Einav et al. | 601/33 |

FOREIGN PATENT DOCUMENTS

JP    2004/317784 A    11/2004

OTHER PUBLICATIONS

Goble et al., "Development of upper limb proprioceptive accuracy in children in adolescence" Jul. 25, 2005 pp. 155-170 as submitted by applicant.*
Goble, D.J., et al., "Development of upper limb proprioceptive accuracy in children and adolescents", Human Movement Science, 24: 155-170 (2005).
Extended European Search Report (EESR) for European Patent Application No. 07816119.7 dated Jul. 4, 2011.

(Continued)

*Primary Examiner* — Max Hindenburg
*Assistant Examiner* — Renee Danega
(74) *Attorney, Agent, or Firm* — Stephen J. Scribner

(57) ABSTRACT

This invention relates to a method and apparatus for assessing proprioception in a subject. One embodiment of an apparatus of the invention comprises two articulating members attachable to a pair of limbs of a subject, and provides data relating to geometry and/or location and/or motion of each limb in 2- or 3-dimensional space. The apparatus may include means for monitoring gaze direction. The apparatus may comprise a robotic linkage. One embodiment of the method comprises obtaining data relating to the geometry and/or location and/or motion of the limbs, or portions thereof, of a subject as the subject performs a matching task. Another embodiment comprises obtaining data relating to the location of a limb of a subject, together with data relating to gaze direction as the subject looks toward the perceived location of limb.

9 Claims, 10 Drawing Sheets

OTHER PUBLICATIONS

Alvemalm, A., et al., "Measurement of shoulder joint kinaesthesia", Manual Therapy, 1: 140-145 (1996).

Carey, L.M., et al., "Impaired limb position sense after stroke: A quantitative test for clinical use", Arch. Phys. Med. Rehabil., 77: 1271-1278 (Dec. 1996).

Carignan, C., et al., "Design of an Arm Exoskeleton with Scapula Motion for Shoulder Rehabilitation", 12th Int. Conference Adv. Robotics, ICAR '05 Proc., 524-531 (2005).

Elfant, I.L., "Correlation between kinesthetic discrimination & manual dexterity", Am. J. of Occup. Ther., 31(1): 23-28 (Jan. 1977).

Fry-Welch, D., et al., "Age-related changes in upper extremity kinesthesis", Physical & Occupational Therapy in Geriatrics, 20(3/4): 137-154 (2002).

International Search Report PCT/CA2007/001969, Feb. 5, 2009.

Kiguchi, "Design and Control of an Exoskeleton System for Human Upper-Limb Motion Assist", Proc.IEEE/ASME Int.Con.Adv.Intelligent Mechatronics (AIM 2003) 926-931 (2003).

Lönn, J., et al., "Reliability of position sense testing assessed with a fully automated system", Clinical Physiology, 20(1): 30-37 (2000).

Lord, R., et al., "Kinaesthetic sensitivity of normal and clumsy children", Developmental Medicine and Child Neurology, 29: 720-725 (1987).

Sanchez, R., et al., "Monitoring Functional Arm Movement for Home-Based Therapy after Stroke", Proc. 26th Ann. Int. Conference of the IEEE EMBS, 4787-4790 (2004).

Scott, S.H., "Apparatus for measuring and perturbing shoulder and elbow joint positions and torques during reaching", Journal of Neuroscience Methods, 89: 119-127 (1999).

* cited by examiner

METHOD AND APPARATUS FOR ASSESSING PROPRIOCEPTIVE FUNCTION

RELATED APPLICATIONS

This application claims the benefit of the filing date of U.S. Provisional Patent Application No. 60/856,015, filed on Nov. 2, 2006, the contents of which are incorporated herein by reference in their entirety.

FIELD OF THE INVENTION

This invention relates to a method and apparatus for detecting, quantifying, and/or treating impaired processing of sensory information related to limb proprioception (position sense and kinesthesia) and motor control.

BACKGROUND OF THE INVENTION

Sensory information from the limb provided by mechanoreceptors in muscles, joints, and the skin is used for a broad range of sensory and motor functions. In particular, this sensory information combined with other sensory modalities, such as vision, and internal feedback of motor commands provides perceptual information relating to the body and limbs (Haggard and Wolpert, 2005), including position sense and kinesthesia. These perceptual features are sometimes called body scheme or body image.

Sensory feedback from the limb is also important for correcting errors in motor performance, referred to as on-line control (Scott, 2004). While the short-latency spinal reflex parallels joint velocities, it has been shown that the long-latency response (~80 ms) involves limb mechanics (Soechting and Lacquiniti, 1988) and is adaptable so as to incorporate the influence of mechanical loads (Burdet et al., 2001; Wang et al., 2001). Also, sensory information is used to direct context-dependent motor responses. For example, it has been shown that small perturbations that push the limb may elicit rapid push or pull motor responses depending on the cued behaviour (Evarts and Tanji, 1976). Thus sensory information is important for a broad range of motor actions.

Another important role for sensory information for motor control is for motor adaptation. For example, during repeated trials of a task an unexpected mechanical load may initially alter limb trajectory. However, subjects are able to modify their motor patterns after a few trials with the load, so that the original limb trajectory is substantially recovered (Lackner and DiZio, 1994; Shadmehr and Mussa-Ivaldi, 1994). If the load is abruptly removed, there is again a deviation in the limb trajectory, and the deviation is a mirror reflection of the perturbation observed when the load was introduced. Recent research suggests that this adaptive process for updating motor patterns for a given movement is strongly dependent on errors in motor performance from the preceding trial (Schiedt et al., 2001), illustrating how sensory feedback from a given movement influences the very next movement.

Clinical assessment of sensorimotor and cognitive function plays a crucial role in all aspects of treating patients, from diagnosing a specific disease or injury, to managing and monitoring rehabilitation strategies to ameliorate dysfunction (Van Dursen and Brent, 1997). The most common clinical assessment technique for proprioception is the Nottingham Sensory Assessment—Revised (Lincoln, 1998). In this technique the clinician positions a joint of the subject's affected limb and asks the subject to mirror the position with the unaffected limb, and then scores the subject's performance (score 0 to 3). In the thumb localizing test (TLT), which is a general proprioceptive test, an examiner holds the affected hand of a subject at a position, and has the subject grasp the thumb of the affected hand with the unaffected hand, with his/her eyes closed (Hirayama et al., 1999; Rand et al., 2001). This is repeated with the affected hand held at different positions, and the subject's performance scored according to a scale (score 0 to 3).

The major challenge with these proprioceptive tests is that they are inherently subjective and have limited resolution. A recent study concluded that the Fugle-Meyer Assessment sensation sub-scale (also based on subjective measures) could not be recommended for clinical use because it showed a significant ceiling effect and low validity and responsiveness to clinically meaningful change (Lin et al., 2004). The ceiling effect implies that many patients attain full score without necessarily having intact sensation.

Some quantitative tests of position sense measure the ability of subjects to actively or passively attain some limb joint angle (Alvemalm et al., 1996; Carey et al., 1996; Elfant, 1977; Carey et al., 2002). For example, the Wrist Position Sense Test (WPST) provides a quantitative measure of wrist position sense in individuals who have had a stroke (Carey et al., 1996; Carey et al., 2002). The WPST is a box-like apparatus with two protractor scales. There is a pointer on top of the box above a protractor (visible to the subject), aligned with the axis of movement of the wrist. There is also an examiner protractor scale, inside the box (hidden from the subject). The subject places an arm in a forearm splint and hand splint which is attached to a lever allowing for movement at the wrist. The examiner imposes wrist movement by moving the lever to different test positions at a relatively constant speed. The subject is unable to see his/her wrist position and the lever. The subject indicates his/her judgment of wrist position by moving the pointer with the other hand or by asking the examiner to move the pointer until he/she believes that it coincides with the wrist angle. The examiner notes the difference between the actual angle (from the hidden protractor) and the perceived angle (from the pointer). Similarly, the work of Brown et al. at the University of Michigan provides apparatus that interfaces with the subject's hand to evaluate proprioception (http://www.kines.umich.edu/research/chmr/mcl.html).

Another example of such a test is the Fully-Automated System by Lonn et al. (1999), which was used to assess position sense at the shoulder in one movement direction. A motorized rig device with a servomotor and a gearbox for different starting and target positions was used. Earphones were given to subjects to receive verbal instructions and minimize auditory cues. The motor rotates the rig to a pre-designated target position and then returns the rig to the starting position. The subject then attempts to replicate the target position and presses a button which registers the matching position. The score is measured as the degree of error between each response and target.

Finally, the Proprioceptometer was designed to quantify position sense changes in the metacarpophalangeal joint (Wycherley et al., 2005). Similar to the WPST, it is a box-like apparatus with a protractor and silhouette (arrow) on top (visible to subject), and an examiner's scale in the middle (hidden from subject). The subject's index finger is isolated in the box out of the subject's view. The subject is asked to match their index finger with the position of the silhouette which is moved in a predetermined sequence. The examiner notes the difference between the perceived and actual angles. In the study by Wycherley et al. (2005), 12 healthy subjects were tested and excellent test-retest reliability was found with this group. However, its validity is unknown. The strengths of this test include the fact that it is a portable device and can be administered in a short time frame (15 minutes). However, a weakness of this test is that individuals with significant deformity of the hand may have difficulty using the apparatus.

A problem with all of the quantitative systems discussed above is that they are limited to motion in a single dimension, and of a single a joint. However, the ability to generate whole-limb motor tasks requires sensory function at multiple joints. Further, impairments may not only reflect sensory impairments at individual joints, but also reflect impairments in the relationship between the limb and its location in space relative to the body (Haggard and Wolpert, 2005).

A number of devices have been proposed for measuring motor performance of the limb. For example, U.S. Pat. No. 6,155,993, issued Dec. 5, 2000 to Scott, relates to a robotic device that can quantify limb movement including motion of the hand and joints and provides joint-based forces to resist limb movement. U.S. Pat. No. 5,210,772, issued Apr. 13, 1993 to Maxwell, relates to a complex linkage which attaches to a subject's limb, and provides forces to resist limb movement. U.S. Pat. No. 5,466,213, issued Nov. 14, 1995 to Hogan et al., relates to a robotic therapist consisting of a computer-controlled mechanical linkage that interfaces with a subject's hand and guides the arm through a range of movement. U.S. Pat. No. 5,830,160, issued Nov. 3, 1998 to Reinkensmeyer relates to a system consisting of a guide that permits limb movement along a linear path. U.S. Pat. No. 6,692,449, issued Feb. 17, 2004 to Brown, relates to a system for assessing limb position of a moving limb. While these systems may be useful in quantifying motor performance or provide motor rehabilitation programs for individuals with impaired movement of limbs, they do not readily provide information relating to sensory impairments of the limb.

SUMMARY OF THE INVENTION

According to one aspect, the invention provides an apparatus for obtaining proprioception data for a limb of a subject, comprising: a first articulating member having first coupling means for coupling a first limb of a pair of limbs of the subject thereto, the first articulating member moveable in 2- or 3-dimensional space and adapted for maintaining the limb in a desired geometry and/or at a desired location and/or for moving the limb through a desired motion in 2- or 3-dimensional space; a second articulating member having second coupling means for coupling a second limb of said pair of limbs of the subject thereto, the second articulating member adapted for being moved by the second limb in 2- or 3-dimensional space; means for obtaining data relating to geometry and/or location and/or motion of the first limb in 2- or 3-dimensional space; and means for obtaining data relating to geometry and/or location and/or motion of the second limb in 2- or 3-dimensional space.

The first articulating member may include a drive system such that the first articulating member guides the first limb to a position and/or location in 2- or 3-dimensional space. In another embodiment, the first articulating member and the second articulating member each comprise a mechanical linkage. In another embodiment, the first articulating member and the second articulating member respectively comprise first and second mechanical linkages, each linkage having four links connected at four joints, each joint having articulation about an axis, the four axes of articulation being substantially parallel; wherein the first limb coupling means and the second limb coupling means each maintain alignment of centers of rotation of two joints of a limb with centers of rotation of two joints of the linkage.

The means for obtaining data relating to geometry and/or location and/or motion of the first limb in 2- or 3-dimensional space may include means for obtaining data respecting angular position of at least one of said joints of said first linkage; and the means for obtaining data relating to position and/or location and/or motion of the second limb in 2- or 3-dimensional space may include means for obtaining data respecting angular position of at least one of said joints of said second linkage.

The first and second limbs may be the arms or the legs. Where the first and second limbs are arms, the first and second coupling means couple the forearm and the upper arm to links of respective linkages such that centers of rotation of the shoulder joint and elbow joint of each arm are maintained in alignment with centers of rotation of two axes of the first and second linkages.

The apparatus may further comprise means for comparing data relating to geometry and/or location and/or motion of the first limb in 2- or 3-dimensional space with data relating to geometry and/or location and/or motion of the second limb in 2- or 3-dimensional space.

According to another aspect, the invention provides a method for obtaining proprioception data for a limb of a subject, comprising: providing a first articulating member having first coupling means for coupling a first limb of a pair of limbs of the subject thereto, the first articulating member moveable in 2- or 3-dimensional space and adapted for maintaining the limb in a desired geometry and/or at a desired location and/or for moving the limb through a desired motion in 2- or 3-dimensional space; providing a second articulating member having second coupling means for coupling a second limb of said pair of limbs of the subject thereto, the second articulating member adapted for being moved by the second limb in 2- or 3-dimensional space; obtaining data relating to geometry and/or location and/or motion of the first limb in 2- or 3-dimensional space; and obtaining data relating to geometry and/or location and/or motion of the second limb in 2- or 3-dimensional space.

The data for the first limb may relate to location of a portion of the first limb in 2- or 3-dimensional space, and data for the second limb may relate to location of a portion of the second limb in 2- or 3-dimensional space. In one embodiment, the portion of the second limb corresponds to the portion of the first limb. In another embodiment, data for the first limb relates to geometry of the first limb in 2- or 3-dimensional space, and data for the second limb relates to geometry of the second limb in 2- or 3-dimensional space.

The data for the first limb may include data relating to a trajectory of the first limb in 2- or 3-dimensional space, and data for the second limb may include data relating to a trajectory of the second limb in 2- or 3-dimensional space.

Another aspect of the invention relates to a method for assessing proprioception in a subject, comprising: obtaining proprioception data for the subject according to the method described herein, the subject performing a matching task; and comparing the data obtained for the two limbs; wherein the comparison provides information about proprioception relating to the subject's said limbs.

Another aspect of the invention relates to a method for diagnosing or detecting brain injury and/or a neurological disorder in a subject, comprising: obtaining proprioception data for the subject according to the method described herein, the subject performing a matching task; and comparing the data obtained for the two limbs; wherein the comparison provides information about brain injury and/or a neurological disorder in the subject.

Another aspect of the invention relates to a method for detecting a neural and/or muscular problem associated with impaired movement of a limb of a subject, comprising: obtaining proprioception data for the subject according to the method described herein, the subject performing a matching task; and comparing the data obtained for the two limbs; wherein the comparison provides information about a neural and/or muscular problem associated with impaired movement of a limb of the subject.

In a further embodiment the invention relates to an apparatus for obtaining proprioception data for a limb or portion thereof of a subject, comprising: a first articulating member having first coupling means for coupling a first limb of a pair of limbs of the subject thereto, the first articulating member moveable in 2- or 3-dimensional space and adapted for maintaining the limb in a desired geometry and/or at a desired location and/or for moving the limb through a desired motion in 2- or 3-dimensional space; a second articulating member having second coupling means for coupling a second limb of said pair of limbs of the subject thereto, the second articulating member adapted for being moved by the second limb in 2- or 3-dimensional space; means for obtaining data relating to geometry and/or location and/or motion of the first limb in 2- or 3-dimensional space; and means for obtaining data relating to geometry and/or location and/or motion of the second limb in 2- or 3-dimensional space.

The first articulating member may include a drive system such that the first articulating member guides the first limb to a position and/or location and/or through a motion in 2- or 3-dimensional space.

The apparatus may further comprise means for comparing data relating to geometry and/or location and/or motion of the first limb in 2- or 3-dimensional space with data relating to geometry and/or location and/or motion of the second limb in 2- or 3-dimensional space.

In a further embodiment the invention relates to a method for obtaining proprioception data for a limb or portion thereof of a subject, comprising: coupling a first limb of a pair of limbs of the subject to a first articulating member, the first articulating member moveable in 2- or 3-dimensional space and adapted for maintaining the limb in a desired geometry and/or at a desired location and/or for moving the limb through a desired motion in 2- or 3-dimensional space; coupling a second limb of said pair of limbs of the subject to a second articulating member, the second articulating member adapted for being moved by the second limb in 2- or 3-dimensional space; obtaining data relating to geometry and/or location and/or motion of the first limb in 2- or 3-dimensional space; and obtaining data relating to geometry and/or location and/or motion of the second limb in 2- or 3-dimensional space.

The data for the first limb may include data relating to a position, location, geometry, and/or trajectory of the first limb or portion thereof in 2- or 3-dimensional space, and data for the second limb may include data relating to a position, location, geometry, and/or trajectory of the second limb or portion thereof in 2- or 3-dimensional space.

In a further embodiment the invention relates to a method for assessing proprioception in a subject, comprising: obtaining proprioception data for the subject according to the method described above, the subject performing a matching task; and comparing the data obtained for the two limbs; wherein the comparison provides information about proprioception relating to the subject's limbs.

In a further embodiment the invention relates to a method for diagnosing or detecting brain injury and/or a neurological disorder in a subject, comprising: obtaining proprioception data for the subject according to the method described above, the subject performing a matching task; and comparing the data obtained for the two limbs; wherein the comparison provides information about brain injury and/or a neurological disorder in the subject.

In a further embodiment the invention relates to a method for detecting a neural and/or muscular problem associated with impaired movement of a limb of a subject, comprising: obtaining proprioception data for the subject according to the method of claim 4, the subject performing a matching task; and comparing the data obtained for the two limbs; wherein the comparison provides information about a neural and/or muscular problem associated with impaired movement of a limb of the subject.

In a further embodiment the invention relates to an apparatus for obtaining proprioception data for a limb or portion thereof of a subject, comprising: an articulating member having coupling means for coupling a first limb of a pair of limbs of the subject thereto, the articulating member moveable in 2- or 3-dimensional space and adapted for maintaining the first limb in a desired geometry and/or at a desired location and/or for moving the first limb through a desired motion in 2- or 3-dimensional space; means for obtaining data relating to geometry and/or location and/or motion of the first limb or portion thereof in 2- or 3-dimensional space; and means for monitoring the subject's gaze direction and relating the subject's gaze direction to the geometry and/or location and/or motion of the first limb or portion thereof in 2- or 3-dimensional space.

The articulating member may a drive system such that the articulating member guides the first limb to a position and/or location and/or through a motion in 2- or 3-dimensional space.

The apparatus may further comprise a second articulating member having second coupling means for coupling a second limb of said pair of limbs of the subject thereto, the second articulating member adapted for being moved by the second limb in 2- or 3-dimensional space; and means for obtaining data relating to geometry and/or location and/or motion of the second limb or portion thereof in 2- or 3-dimensional space.

In a further embodiment the invention relates to a method for obtaining proprioception data for a limb or portion thereof of a subject, comprising: coupling a first limb of a pair of limbs of the subject to an articulating member, the articulating member maintaining the first limb in a desired geometry and/or at a desired location in 2- or 3-dimensional space, and/or moving the first limb through a desired motion in 2- or 3-dimensional space, while preventing the subject from seeing the first limb; obtaining data relating to geometry and/or location and/or motion of the first limb or portion thereof in 2- or 3-dimensional space; monitoring the subject's gaze direction as the subject is looking toward the perceived location of the first limb or portion thereof; and relating the subject's gaze direction to the geometry and/or location and/or motion of the first limb or portion thereof in 2- or 3-dimensional space.

The method may further comprise: coupling a second limb of said pair of limbs of the subject to a second articulating member, the second articulating member adapted for being moved by the second limb in 2- or 3-dimensional space; and obtaining data relating to geometry and/or location and/or motion of the second limb or portion thereof in 2- or 3-dimensional space when the subject moves the second limb to the perceived geometry and/or location of the first limb, or through the perceived motion of the first limb. The method may further include monitoring gaze direction as the subject looks toward the position, location and/or movement of the second limb or portion thereof in 2- or 3-dimensional In a further embodiment the invention relates to a method for assessing proprioception in a subject, comprising: obtaining proprioception data for the subject according to the method described above, the subject performing a matching task; wherein relating the subject's gaze direction to the perceived geometry and/or location and/or motion of the first limb or portion thereof in 2- or 3-dimensional space provides information about proprioception associated with the subject's limbs.

In a further embodiment the invention relates to a method for diagnosing or detecting brain injury and/or a neurological disorder in a subject, comprising: obtaining proprioception data for the subject according to the method described above, the subject performing a matching task; wherein relating the subject's gaze direction to the perceived geometry and/or location and/or motion of the first limb or portion thereof in 2- or 3-dimensional space provides information about brain injury and/or a neurological disorder in the subject.

In a further embodiment the invention relates to a method for detecting a neural and/or muscular problem associated with impaired movement of a limb of a subject, comprising: obtaining proprioception data for the subject according to the method described above, the subject performing a matching task; wherein relating the subject's gaze direction to the perceived geometry and/or location and/or motion of the first limb or portion thereof in 2- or 3-dimensional space provides information about a neural and/or muscular problem associated with impaired movement of a limb of the subject.

In one embodiment moving the first limb may comprise moving the limb manually by a person other than the subject. In another embodiment moving the first limb may comprise moving the limb using a robotic linkage. The method may further comprise the subject performing a matching task; and obtaining data relating to the geometry and/or location and/or motion of the subject's second limb or corresponding portion thereof.

Another aspect of the invention relates to an apparatus for obtaining proprioception data for a limb of a subject, comprising: a first marker that attaches to a first limb of a pair of limbs of the subject, the first marker moveable in 2- or 3-dimensional space; a second marker that attaches to a second limb of said pair of limbs of the subject, the second marker moveable in 2- or 3-dimensional space; means for detecting the first and second markers in 2- or 3-dimensional space; wherein detecting comprises determining location and/or motion of the first and second markers in 2- or 3-dimensional space. The apparatus may further comprise means for comparing location and/or motion of the first and second markers in 2- or 3-dimensional space.

Another aspect of the invention relates to an apparatus for obtaining proprioception data for a limb of a subject, comprising: a first group of markers that attach to a first limb of a pair of limbs of the subject, each marker of the first group of markers being independently moveable in 2- or 3-dimensional space; a second group of markers that attach to a second limb of a pair of limbs of the subject, each marker of the second group of markers being independently moveable in 2- or 3-dimensional space; means for detecting each marker of the first and second groups of markers in 2- or 3-dimensional space; wherein detecting comprises determining location and/or geometry and/or motion of the first and second markers in 2- or 3-dimensional space; wherein each group of markers comprises at least two markers. The apparatus may further comprise means for comparing location and/or geometry and/or motion of the first and second groups of markers in 2- or 3-dimensional space.

Another embodiment relates to an apparatus for obtaining proprioception data for a limb or portion thereof of a subject, comprising: one or more wired or wireless markers adapted to attach to a first limb of a pair of limbs of the subject, the one or more markers movable in 2- or 3-dimensional space; one or more wired or wireless markers adapted to attach to a second limb of the pair of limbs of the subject, the one or more markers movable in 2- or 3-dimensional space; and means for detecting position, location, and/or movement of each of the markers in 2- or 3-dimensional space; wherein position, location, and/or movement of a said marker in 2- or 3-dimensional space corresponds to position, location, and/or movement in 2- or 3-dimensional space of the portion of the limb to which the said marker is attached.

According to this embodiment, the one or more markers may be passive markers, active markers, and/or combinations thereof. The apparatus may further comprise at least one mechanical linkage that attaches to a limb.

Another embodiment relates to an apparatus for obtaining proprioception data for a limb or portion thereof of a subject, comprising: means for obtaining data relating to geometry and/or location and/or motion of the limb or portion thereof in 2- or 3-dimensional space without the subject seeing the geometry and/or location and/or motion of the limb; a display for displaying geometry and/or location and/or motion of the subject's limb or portion thereof in 2- or 3-dimensional space; and means for indicating on the display the geometry and/or location and/or motion of the limb or portion thereof as perceived by the subject.

According to this embodiment, the means for obtaining data relating to geometry and/or location and/or motion of the limb or portion thereof in 2- or 3-dimensional space may include an articulating member having coupling means for coupling the subject's limb thereto. The means for obtaining data relating to geometry and/or location and/or motion of the limb or portion thereof in 2- or 3-dimensional space may include one or more wired or wireless markers adapted to attach to a first limb of a pair of limbs of the subject, the one or more markers movable in 2- or 3-dimensional space; and means for detecting position, location, and/or movement of each of the markers in 2- or 3-dimensional space.

Another embodiment relates to an apparatus for obtaining proprioception data for a limb or portion thereof of a subject, comprising: one or more wired or wireless markers adapted to attach to a first limb of a pair of limbs of the subject, the one or more markers movable in 2- or 3-dimensional space; means for detecting position, location, and/or movement of each of the markers in 2- or 3-dimensional space; and means for monitoring the subject's gaze direction and relating the subject's gaze direction to the position, location and/or movement of the limb or portion thereof in 2- or 3-dimensional space as detected from the one or more markers.

Another aspect of the invention relates to a method for obtaining proprioception data for a limb or portion thereof of a subject. In one embodiment, the method comprises attaching one or more wired or wireless markers to a first limb of a pair of limbs of the subject, the one or more markers movable in 2- or 3-dimensional space; attaching one or more wired or wireless markers to a second limb of the pair of limbs of the subject, the one or more markers movable in 2- or 3-dimensional space; detecting position, location, and/or movement of each of the markers for each limb in 2- or 3-dimensional space, wherein position, location, and/or movement of a said marker in 2- or 3-dimensional space corresponds to position, location, and/or movement in 2- or 3-dimensional space of the portion of the limb to which the said marker is attached; and comparing position, location, and/or movement of the first limb and the second limb in 2- or 3-dimensional space; wherein a result of the comparison provides proprioception data for a said limb or portion thereof.

Another embodiment relates to a method for obtaining proprioception data for a limb or portion thereof of a subject, comprising: obtaining data relating to geometry and/or location and/or motion of the limb or portion thereof in 2- or 3-dimensional space without the subject seeing the geometry and/or location and/or motion of the limb; displaying geometry and/or location and/or motion of the subject's limb or portion thereof in 2- or 3-dimensional space; and indicating on the display the geometry and/or location and/or motion of the limb or portion thereof as perceived by the subject; wherein a comparison of the actual and perceived geometry and/or location and/or motion of the limb or portion thereof in 2- or 3-dimensional space provides proprioception data for a said limb or portion thereof.

Another embodiment relates to a method for obtaining proprioception data for a limb or portion thereof of a subject, comprising: attaching to a first limb of a pair of limbs of the subject one or more wired or wireless markers, the one or more markers movable in 2- or 3-dimensional space; detecting position, location, and/or movement of each of the markers in 2- or 3-dimensional space; monitoring the subject's gaze direction as the subject looks at the perceived position, location and/or movement of the limb or portion thereof in 2- or 3-dimensional; and relating the subject's gaze direction to the position, location and/or movement of the limb or portion thereof in 2- or 3-dimensional space as detected from the one or more markers; wherein relating provides proprioception data for a said limb or portion thereof.

Further aspects of the invention relate to methods for assessing proprioception in a subject, methods for diagnosing or detecting brain injury and/or a neurological disorder in a subject, methods for diagnosing and/or detecting a neural and or muscular problem associated with impaired movement of a limb of a subject, and methods for assessing or detecting impaired body scheme in a subject, such methods including any of the methods and apparatus as described herein.

BRIEF DESCRIPTION OF THE DRAWINGS

Embodiments of the invention will now be described, by way of example, with reference to the accompanying drawings, wherein:

In FIG. 3A, the robotic linkage moved the left arm (paretic in stroke subjects) and subjects matched the geometry with the right arm. Positive X geometry is near the midline and negative is lateral. In FIG. 3B, Y hand location (away more positive) is shown. In FIGS. 3C and 3D, shoulder and elbow angles are shown.

DETAILED DESCRIPTION OF PREFERRED EMBODIMENTS

Figure 1:
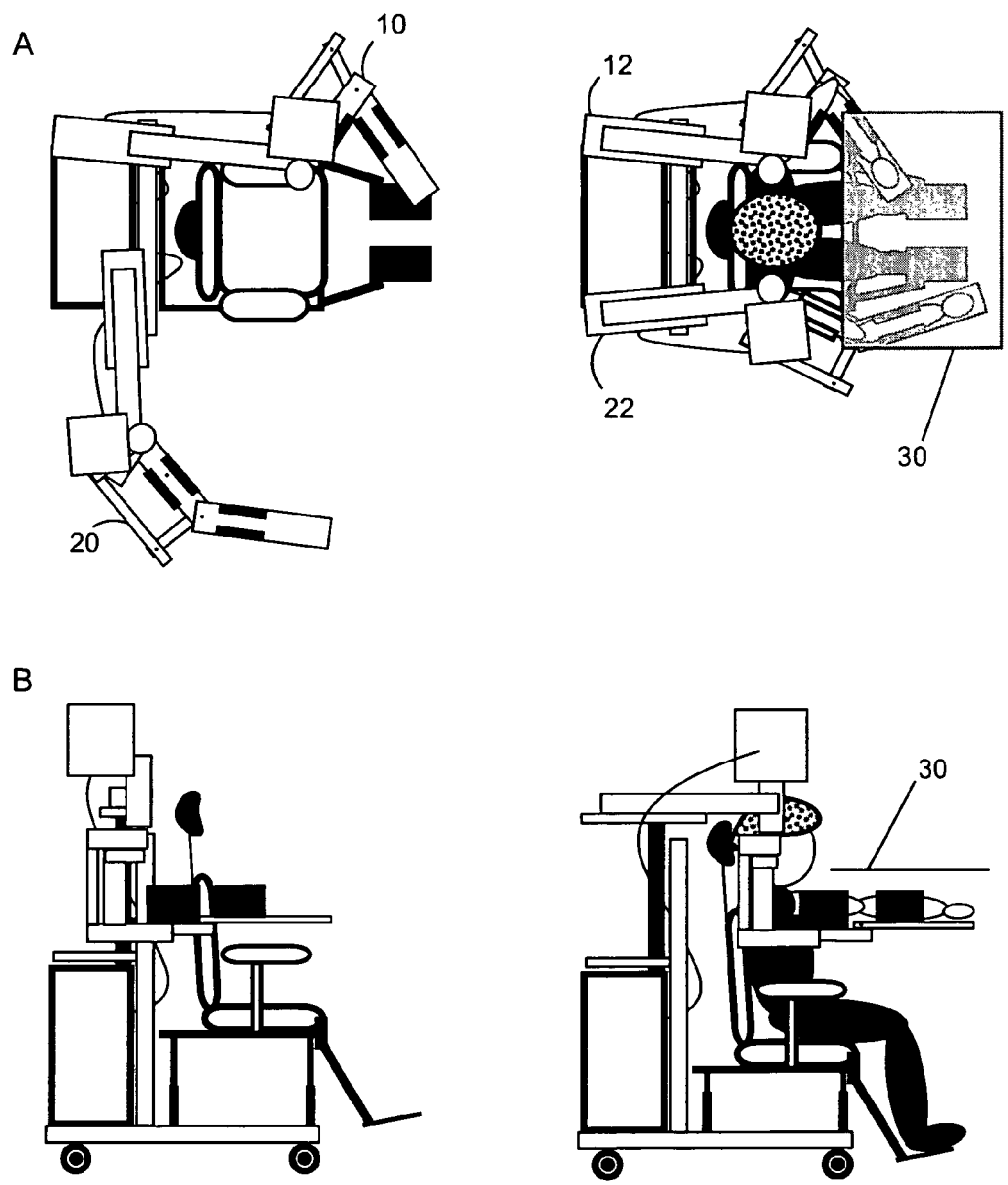
FIGS. 1A and 1B show diagrammatically an apparatus used to assess proprioceptive function according to one embodiment of the invention. On the left (1A and 1B) are overhead and side views of the apparatus alone, wherein the robotic linkages and a seat are shown. On the right (1A and 1B) are overhead and side views showing a subject seated at the apparatus. The apparatus is fully adjustable to accommodate subjects of all sizes, and to permit easy transfer of subjects to and from the apparatus.

Information provided by one or more of proprioceptive, articular, tactile, vestibular, visual, and auditory senses, and/or information related to one or more of kinesthesia, musculature, posture, and equilibrium, as well as information from sense of physical effort, information generated from motor commands, and information from contact with objects and among body parts, contributes to body perception (i.e., a perceptual representation of the body or portion thereof (Lackner, 1988)). This body perception is sometimes called body scheme (or body schema) or body image. For the purpose of this disclosure, the term "proprioception" is used to refer generally to the sense of the relative position or motion (kinesthesia) of the body or portion thereof, as may be obtained from any such perceptual information as listed above, and encompasses the terms body scheme (or body schema) and body image. Thus, while the present description focuses on the assessment of the proprioceptive system, it is also recognized that this approach assesses impairments in related concepts such as, but not limited to, body scheme and body image.

When an individual suffers brain injury from stroke, trauma, or the like, there often results an impairment in sensory processing related to one or more limbs (Teasell et al., 2003). Sensory impairments may also lead to difficulties in motor coordination and learning, due to the importance of sensory feedback in these processes. Effective treatment of both sensory and motor impairments may be enhanced with detailed knowledge of the sensory impairments from the limb; however, none of the instruments proposed to date or currently available is capable of providing the required data.

In accordance with a first aspect of the invention, there is provided an apparatus for obtaining data relating to an individual's ability to perceive the location, geometry, and/or motion (e.g., trajectory) of a first limb of a pair, or portion of that limb, in 2- or 3-dimensional space, and the individual's ability to move the other limb to a corresponding location and/or geometry, and/or trajectory in 2- or 3-dimensional space. The apparatus is therefore useful for studying proprioception; that is, position sense and kinesthesia for the proximal limb in individuals. For example, the apparatus may be used to investigate how sensory information respecting a limb is used for a broad range of sensory and motor functions. While the apparatus is useful for obtaining such data from normal, healthy individuals, it is also particularly useful for obtaining such data from individuals with brain injury and/or neurological disorders, as it may aid one or more of diagnosis, treatment, management, and therapy for such individuals.

For purposes of this application, the term "joint position sense" refers to the sense of position of a joint, and the term "kinesthesia" refers to the sense of motion of a body segment (Lackner and DiZio, 2000).

As used herein, the term "geometry" is intended to refer to the posture of a limb; that is, the relative angles of the joints of the limb that result in the limb being held in a particular posture or configuration.

As used herein, the term "location" is intended to refer to a point in space. Such a point may be described within a coordinate system such a Cartesian coordinate system of 2 or 3 axes corresponding to 2- or 3-dimensional space. For a limb, a portion of interest, such as the hand, thumb, or a finger, or a joint of interest, such as the wrist, elbow, or shoulder, occupies a specific location in space at any particular time.

As used herein, the term "gaze direction" or "eye gaze direction" is intended to refer to the direction where a subject is looking.

One embodiment of the apparatus of the invention relates to an instrument that attaches to a pair of limbs of a subject and allows moving the first limb while measuring at least one of motion, location, and geometry of the second limb, or both limbs. The instrument may include first and second portions, for attaching to first and second limbs of the pair of limbs, which portions may or may not be the same or symmetrical. The first limb, or a portion of the first limb, which may also be referred to as the passive limb, is moved into various geometries and/or locations in 2- or 3-dimensional space, and/or through a range of motion, passively (i.e., not by the subject moving the first limb). Movement of the first limb may be achieved by the clinician or investigator moving the limb manually, or, in the case of the apparatus being motorized, the apparatus guiding the limb. In the latter case, the apparatus may be computer controlled and programmed to guide the limb through a series of motions, geometries, and/or locations in 2- or 3-dimensional space. After the first limb has completed the desired motion or has come to rest in a desired location and/or geometry, the subject then attempts to mimic or parallel that motion, location, and/or geometry with the second limb. This may be referred to as a "matching task". The apparatus provides quantitative information on the ability of a subject to perceive the motion, geometry, and/or location of the first (passive) limb and the ability to use that information to match that motion, geometry, and/or location with the second limb.

Thus, in one generalized embodiment the invention may be an apparatus for obtaining proprioception data for a limb or portion thereof of a subject, comprising a first articulating member having first coupling means for coupling a first limb of a pair of limbs of the subject thereto, the first articulating member moveable in 2- or 3-dimensional space and capable of maintaining the limb in a desired geometry and/or at a desired location in 2- or 3-dimensional space; a second articulating member having second coupling means for coupling a second limb of said pair of limbs of the subject thereto, the second articulating member adapted for being moved by the second limb in 2- or 3-dimensional space; means for obtaining data relating to movement, trajectory, geometry, and/or location of the first limb in 2- or 3-dimensional space; and means for obtaining data relating to movement, trajectory, geometry, and/or location of the second limb in 2- or 3-dimensional space.

In another embodiment the apparatus includes one or more wired or wireless markers such as reflectors or tags that attach to a limb at desired points, such as, for example, the shoulder, elbow, wrist, hand, thumb, or hip, knee, ankle, toe, etc. In certain embodiments the markers may be passive, in that they do not produce an output signal. Such markers may reflect light or other signals (e.g., visible light, infra-red, radio waves (RF), etc.) incident upon them, so as to be detectable by a video camera or other suitable device. In other embodiments the markers may be active, in that they produce an output signal using light (e.g., visible light, infra-red) or radio waves (RF), or the like, so as to be detected by a video camera or other suitable device. The output signal may provide information indicative of the marker location in 2- or 3-dimensional space. Such markers allow the geometry, location, and/or trajectory of a limb, or portion thereof, to be monitored in 2- or 3-dimensional space. Detecting a marker may include determining its location in 2- or 3-dimensional space, as in the case of a passive marker, or may include simply receiving the signal from an active marker, the signal providing the location information for that marker. For example, the apparatus may include one such marker attached to a desired portion of a limb, and a single device, such as a video camera, for detecting the marker. Such an apparatus provides information in two degrees of freedom for that marker, and hence for the portion of the limb to which it is attached. Adding a second video camera at an angle different from the first camera provides three degrees of freedom for the marker. Further, adding markers to other portions of the limb provides for monitoring joint angles, limb geometry, and limb trajectory. An apparatus employing such markers may or may not also include a mechanical linkage that attaches to a limb.

In one embodiment, the apparatus may provide data corresponding to only a single portion of a limb. For example, in the case of the limb being an arm, the portion may be a hand, finger, or thumb, or a joint, such as the wrist, elbow, or shoulder, involving 2 or more mechanical degrees of freedom. Here, the apparatus may comprise an "end effector" robotic linkage such as that disclosed in U.S. Pat. No. 5,466,213, issued Nov. 14, 1995 to Hogan et al., which provides information as to the subject's hand location. However, the inventors recognize that a better understanding of proprioceptive function will be gained from more comprehensive information, which may be obtained by considering multiple portions of the limbs, and/or more degrees of freedom. Accordingly, in another embodiment, the apparatus may provide data corresponding to multiple portions of a limb, such as one or more joints of the arm, or the hand and one or more joints of the arm. For planar (i.e., 2-dimensional) operation, such an embodiment may comprise a robotic linkage such as that disclosed in U.S. Pat. No. 6,155,993, issued Dec. 5, 2000 to Scott, and give information about shoulder and elbow angles, and hand location. It will be appreciated, of course, that the invention is not limited to use with the arms, and may also be used for the legs.

In another embodiment, the apparatus provides data in 3 dimensions. For example, the apparatus may comprise a 3-dimensional exoskeleton into which the limbs are coupled. Such an apparatus provides more degrees of freedom and hence more information.

An apparatus according to the invention has clinical and research applications. For example, the apparatus may be used to assess one or more of position sense and kinesthesia. The apparatus may be configured to allow or prevent the subject from seeing either limb or both limbs of the pair of limbs under investigation. Preventing the subject from seeing one or both limbs increases the challenge of the matching task, thereby providing additional information as to the subject's ability, condition, or sensory deficit by quantifying impairment of visual and proprioceptive integration, and body scheme. The apparatus may be used in rehabilitation of subjects suffering from trauma, stroke, or the like.

As noted above, standard clinical assessments of sensory function of limbs do not provide quantitative, objective measures and/or are limited to measurements at a single joint with a single degree of freedom. There is a need for reliable quantitative measures of limb proprioception to supplement traditional clinical measures. An apparatus according to the invention enhances understanding and provides for the diagnosis and treatment of a wide range of impairments related to sensory function of a limb. Using the invention, a wide range of features of the sensory system can be evaluated, including position sense and kinesthesia. Further, use of an apparatus as described herein provides for the evaluation of subjects to develop quantitative standards of normal subjects and provides measures of motor deficits of various patient populations. The results form the basis for programs directed towards, for example, treatment of these disorders, and ongoing evaluation of the effectiveness of therapeutic treatment interventions.

The invention provides the basis for a paradigm to study proprioceptive function of the upper limb. In particular, using the invention normal and abnormal sensory function can be compared and contrasted. The apparatus can move to any prescribed location in space or limb position/configuration (passive limb), and permit the other limb to mirror image location. The apparatus can measure the joint angles and hand position of each limb. The apparatus may also move the limb through a specified trajectory, such that the subject must attempt to perform a parallel motion with the other limb. Such tasks may be performed with or without vision of the passively moved and/or the active limb to observe the interaction between visual and proprioceptive information.

According to another aspect of the invention there is provided a matching task for assessing proprioception in a subject. In one embodiment of the matching task, one limb of a subject is moved to a specific geometry and maintained in that geometry, and the subject's ability to match that geometry with the corresponding limb is assessed. In another embodiment, a portion of one limb of a subject is moved to a specific location and maintained at that location, and the subject's ability to move the same portion of the corresponding limb to the same location, or to a relative location (e.g., about an axis) is assessed. In another embodiment, the above two tasks are combined such that the subject must match both the geometry of the limb and the location of the portion of the limb. In a further embodiment, the task is a moving matching task wherein one limb of a subject is moved through a trajectory, and the subject must match the movement of that trajectory with the corresponding limb, either simultaneously, or after the first limb has stopped moving. This embodiment may include the subject matching the change in geometry of the limb as it moves through the trajectory, or matching the trajectory of only a portion of the limb with the same portion of the corresponding limb.

Another embodiment relates to an apparatus and method in which gaze direction is used to assess sensory deficit in a subject. According to this embodiment, a first limb or portion thereof, such as, for example, the hand, is moved to a location without the subject being able to see the limb or hand. The subject's gaze direction is then monitored as the subject looks toward the perceived location of the limb or hand. The limb may be moved manually, e.g., by a clinician, or robotically, e.g., by a robotic linkage as described above. This task may or may not include the subject reaching, with the corresponding (second) limb, toward the perceived location of the first limb. Information relating to gaze direction may be obtained using techniques known in the art (see, for example, Ariff, 2002; Morimoto et al., 2002; Amir et al., U.S. Patent Application Publication No. 2003/0098954 A1, May 29, 2003), and an apparatus used to obtain proprioceptive data as described herein, such as, for example, a robotic linkage as in FIG. 1, may further include hardware and software as required to obtain gaze direction data. Gaze direction may be obtained in respect of the subject looking at the perceived location of the first limb, the second limb, or both limbs. This aspect provides for separation of the contribution of the ocular motor system and the sensorimotor system to a subject's body scheme and allows for the possibility of isolating a sensory deficit to one of these systems.

Another embodiment relates to an apparatus and method for a matching task wherein markers as described above and gaze direction are used to assess sensory deficit in a subject. According to this embodiment, markers are disposed on a first limb or portion thereof as described above. The limb is moved to a location without the subject being able to see the limb. The subject is then instructed to look toward the location of the limb or portion thereof, and the subject's gaze direction is monitored as the subject looks toward the perceived location of the limb. The limb may be moved manually, e.g., by a clinician, or robotically, e.g., by a robotic linkage as described above. This task may or may not include the subject reaching, with the corresponding limb, toward the perceived location of the first limb. Information relating to the actual position or location of the limb obtained from the markers is then compared with the subject's gaze direction.

A further embodiment relates to an apparatus and a method for a matching task wherein a first limb or portion thereof is moved to a location with or without the subject being able to see the limb, and the subject then uses a joystick, mouse, or other pointing device to move a cursor or other visual indicator to the perceived location of the first limb, there being a virtual reality display (2- or 3-dimensional) capable of displaying the location of a cursor at the perceived location of the first limb. Alternatively, the subject may issue verbal commands to a clinician operating a joystick, mouse or other pointing device to move a cursor or other visual indicator to the perceived location of the first limb. The limb may be moved manually, e.g., by a clinician, or robotically, e.g. by a robotic linkage as described above. This task may or may not include the subject reaching, with the corresponding limb, toward the perceived location, or mirrored location, of the first limb. According to this embodiment the location of the cursor is detected and measured with respect to the actual limb position.

The contents of all references and published patent documents cited throughout this application are hereby incorporated by reference.

The invention is further described by way of the following example, which shall be understood to be non-limiting.

EXAMPLE

The following example describes an embodiment of the invention wherein an apparatus having first and second robotic linkages were configured to attach to the upper arm and forearm portions of first and second arms of a subject. In this example, the ability of control and stroke subjects to perform a bilateral limb matching task was evaluated. This was done without the subjects being able to see their arms. The robotic linkage moved the paretic limb to a spatial location and geometry and the subject was asked to match this limb position and geometry with the non-paretic limb.

It should be noted that the task may also be performed with the apparatus moving the non-paretic limb and the subject actively matching with their paretic limb. As well, this task can be performed with or without vision of either or both limbs.

Apparatus

The apparatus consisted of a mechanical linkage attached to the upper arm and forearm of each limb of a subject (see FIGS. 1A and B). This linkage is described in detail in U.S. Pat. No. 6,155,993, issued Dec. 5, 2000 to Scott, and will be described only briefly here. The mechanical linkage 10 or 20 allowed the subject to make combined flexion and extension movements of the shoulder and elbow joints to move his/her hand to any location in the horizontal plane. The linkage can also be mechanically driven to move either limb to any location in the horizontal plane. Each linkage was attached by one of its articulating joints to a rigid structure 12, 22 such as a housing or a support that places it in proper alignment with the subject. In the case of an arm, proper alignment was achieved when the center of rotation of that articulating joint was aligned with the center of rotation of the subject's shoulder. The rigid structure effectively anchored the linkage to a fixed point in space, allowing the linkage to be manipulated about that point, and, when the subject to which the linkage was attached was also held stationary by remaining in a suitable position, such as sitting, any relative movement between the subject's shoulder and that articulating joint was minimized. Friction in the joints of the linkage was minimal. The linkage was adjustable so that its joints could be aligned with the centers of rotation of the shoulder and elbow joints of the subject's arm. Couplings attached to the linkage secured the upper arm and forearm to the linkage. If desired, the couplings could be padded with a suitable material such as closed-cell foam, to improve the subject's comfort. An optional opaque barrier 30 (shown translucent in FIG. 1) may be used to prevent the subject from seeing the limb(s).

The position and motion of the shoulder and elbow joints could be manipulated directly. First and second torque motors (Parker, Compumotor SM233A) were employed, and timing belts connected each motor to the mechanical linkage, such that the first motor acted on the upper arm and the second motor acted indirectly on the forearm. A main computer electrically connected to the motor amplifiers (Parker, Compumotor GV-L3E) via a programmable control card (Delta Tau, PMAC-Lite-PCI) controlled the motors and read data from them.

As can be seen in FIG. 1, the linkage was essentially a parallelogram (i.e., a quadrilateral having both pairs of opposite sides parallel to each other). Couplings secured the upper arm and forearm to the linkage. The positions of couplings were adjustable along the lengths of the respective links to accommodate different-sized subjects.

As will be appreciated from FIG. 1 and the above description, when the arm of a subject is secured to the linkage, the subject can move his/her arm through a wide range of movement within the horizontal plane. This movement may be performed without any loading of any joints of the arm, i.e., with the linkage moving freely. Information concerning arm movement and geometry (i.e., joint angle) was provided by encoders built in to the torque motors used. The encoders (not shown) were electrically connected to the main computer and provided angular position information (i.e., angular position of the motor shaft as it rotates about its axis). The first motor provided direct feedback of shoulder joint angle. Elbow joint angle was computed by subtracting the encoder signal obtained from the first motor from the encoder signal from the second motor. Hand location was calculated using trigonometry from shoulder and elbow joint angles and the measured length of the subject's upper arm and forearm/hand lengths. The motor system also permitted direct control of limb position using servo control.

The main computer read data from various sensors on the apparatus. According to the preferred embodiment, joint angular position was obtained from the motor encoders with a resolution of, for example, 8192 units per revolution. Hand location was computed from the joint angles using trigonometry. It will be appreciated that the apparatus may be combined with other known techniques and equipment to obtain further information about limb geometry or movement. For example, the activity of proximal arm muscles may be measured when the apparatus is used with suitable electromyography (EMG) equipment and techniques.

Data Acquisition

General purpose data acquisition software (Dexterit-E, BKIN Technologies, Kingston, Ontario, Canada) running on the main computer was used as a basis for a data acquisition system. The acquisition program controlled the position of the linkage attached to one limb and monitored motion of both limb linkages at 1 kHz. A data acquisition card (National Instruments, PCI-6071E) provided 32 differential analog signals to monitor signals such as electromyographic activity at 1 kHz.

Results

FIGS. 2 to 2C and 3A to 3D illustrate the ability of a control subject and 2 stroke subjects to match the location and geometry of their affected limb (left arm) with their non-paretic limb (right arm). Data are presented based on right hand position. Nine targets were used, wherein targets 1 to 3 were near the midline and targets 7 to 9 were most lateral. The position of the left hand was mirror transposed and is denoted by the numbers in FIGS. 2A to 2C. Five repeat trials are shown on the left panel (FIGS. 2A to 2C, raw data), whereas the mean and standard deviation across repeat trials are shown on the right panel (FIGS. 2A to 2C) by the open symbols and vertical and horizontal bars. Solid icons show the corresponding position of the left hand, mirror transposed.

Figure 2A:
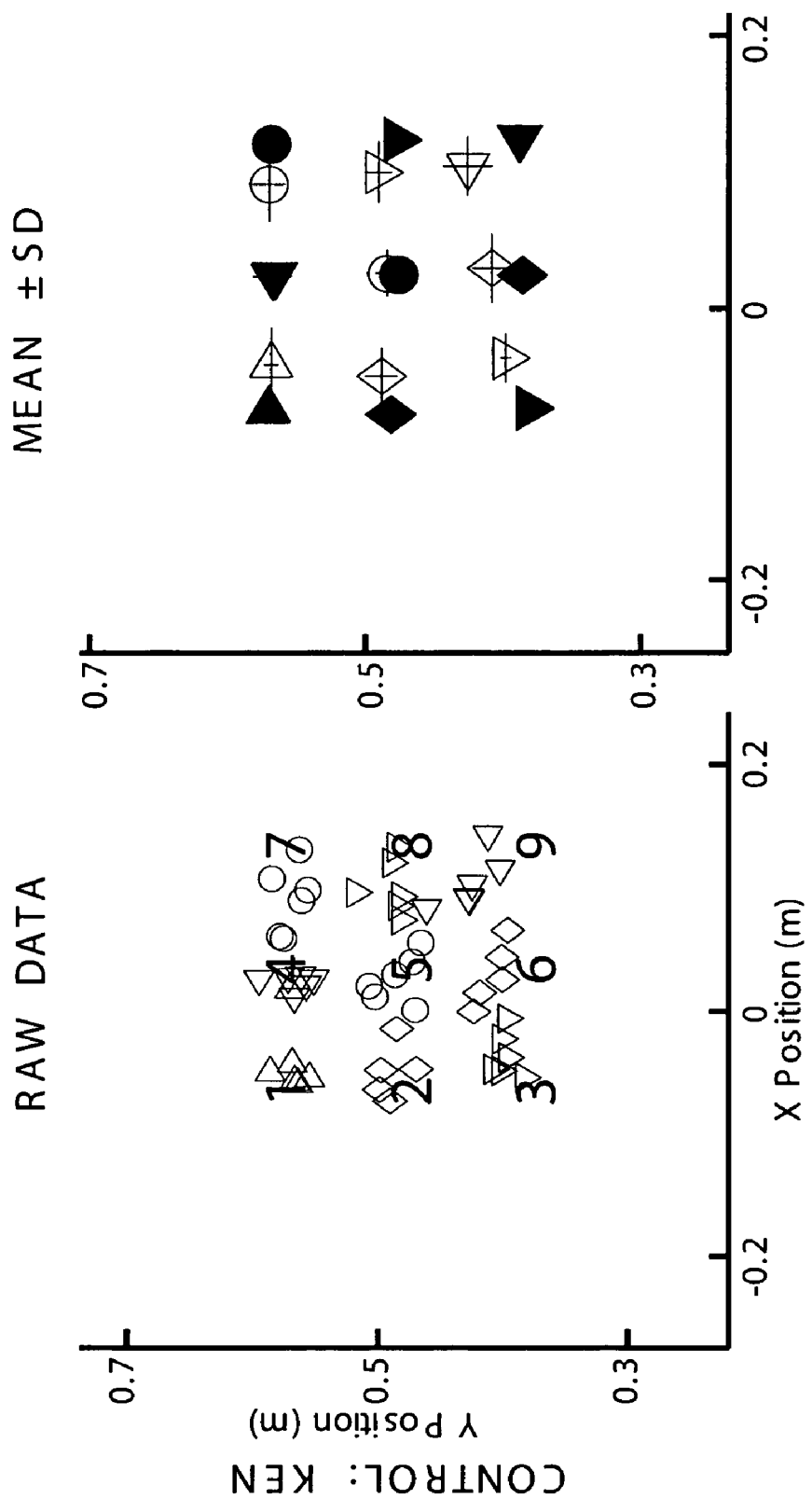
FIGS. 2A to 2C show data obtained with the apparatus of FIG. 1 relating to the ability of a control subject (2A, KEN) and two stroke subjects (2B, CS; and 2C, JLM) to match the location of the left hand with the right hand, for nine hand locations. Data are for five repeats at each location. For the stroke subjects, the left arm was paretic and the right arm was non-paretic. The control subject was consistently better at replicating his hand location with the other hand as compared to the stroke subjects. Stroke subject CS showed a wide dispersion in perceived location of the hand, whereas stroke subject JLM perceived hand locations to be all located near the midline.
Figure 2B:
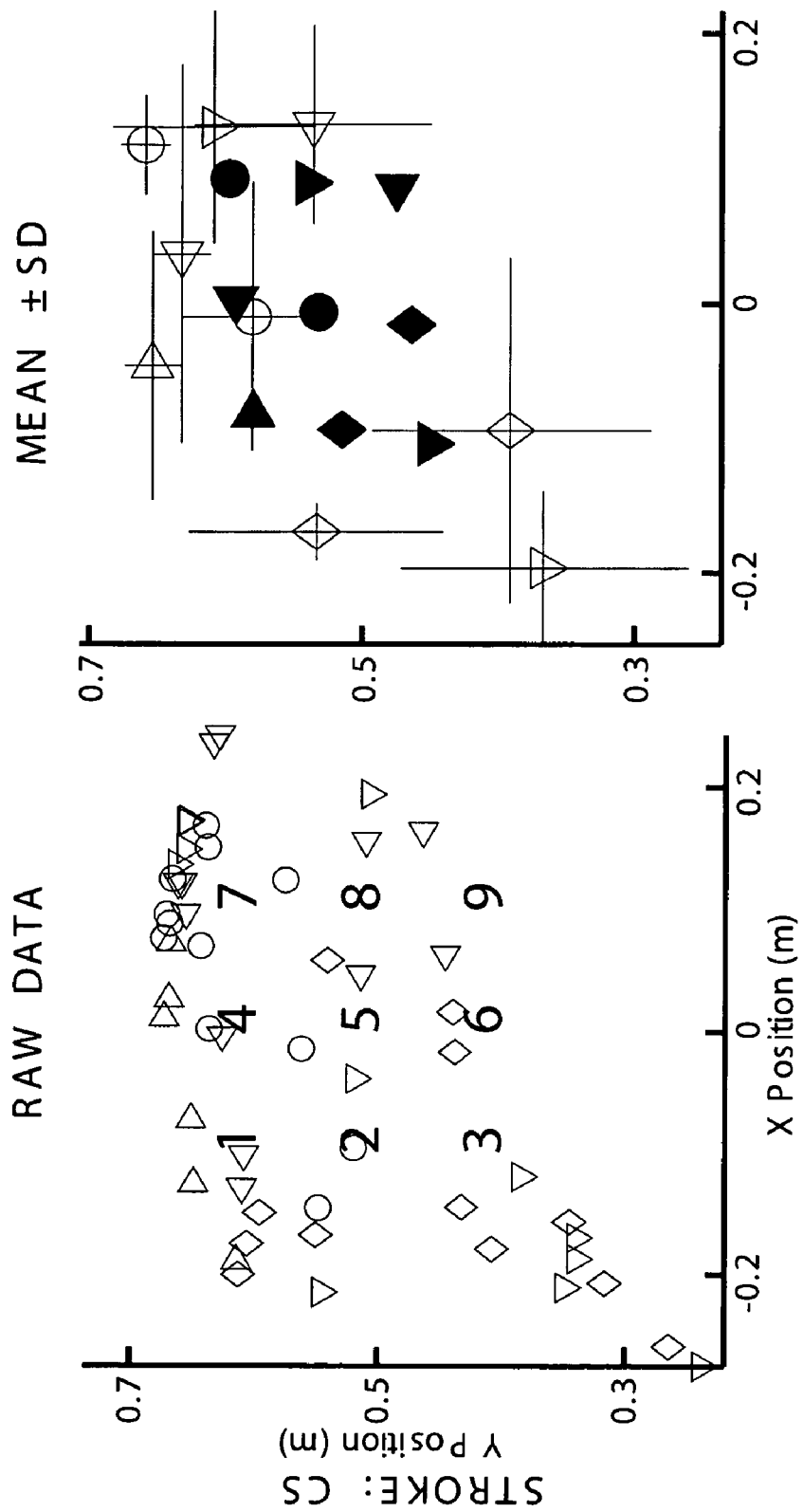
Figure 2C:
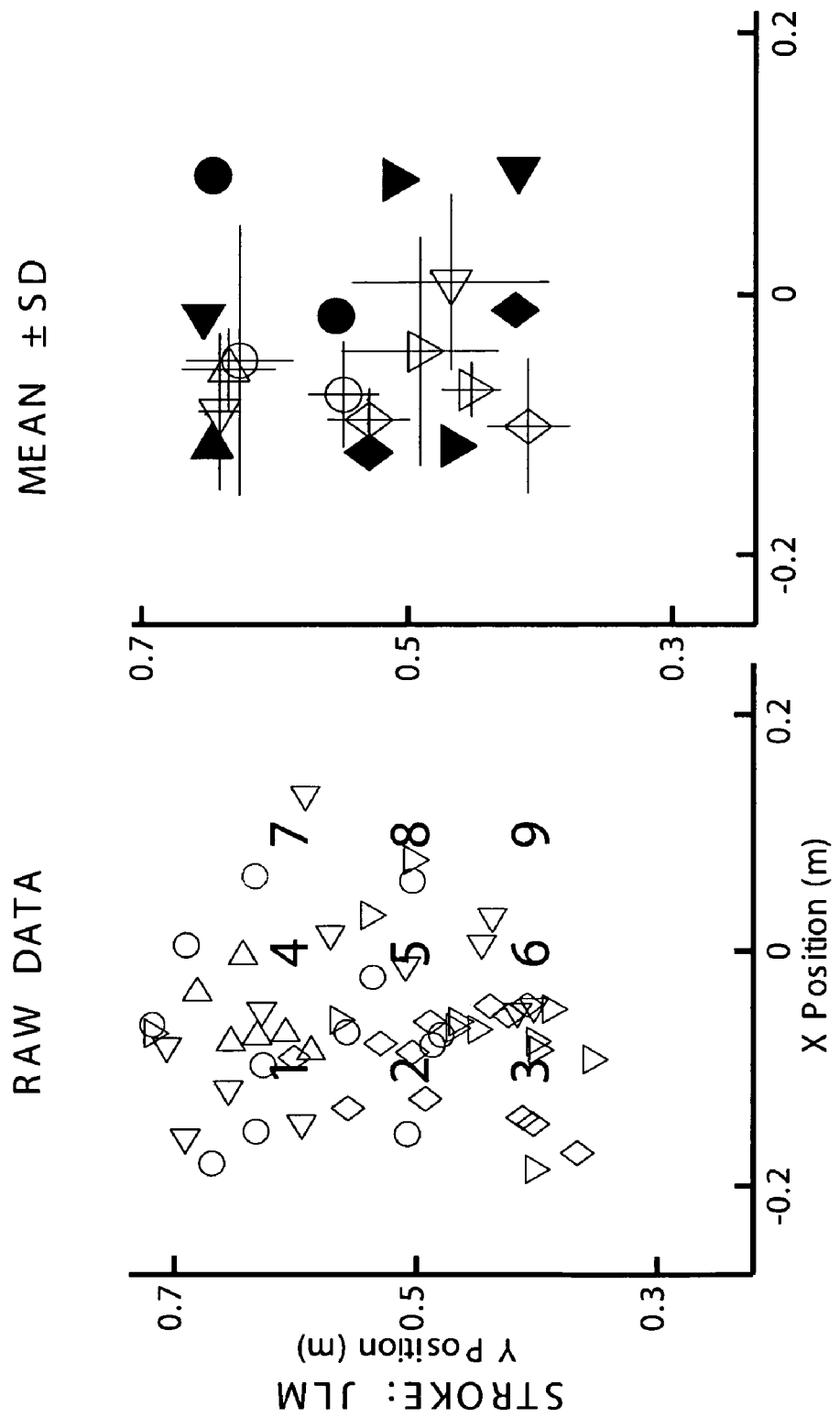
Figure 3A:
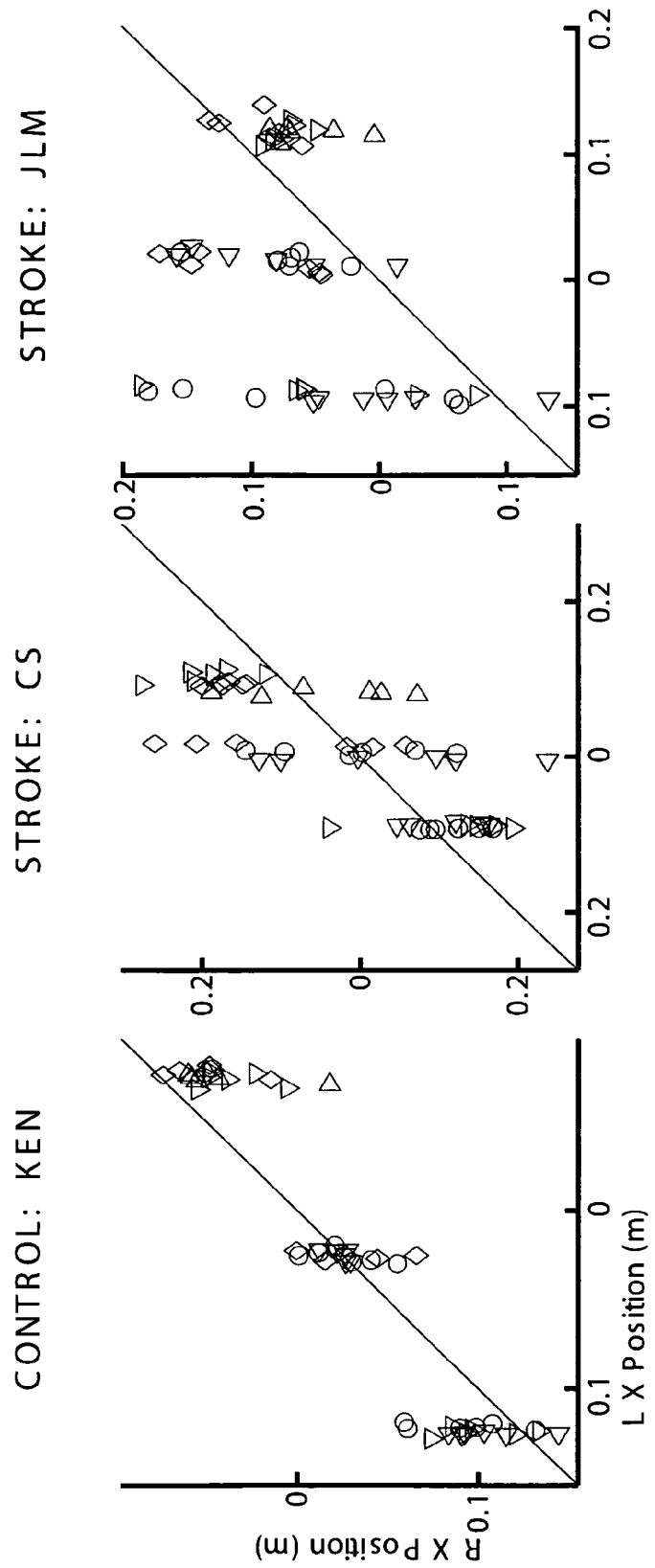
FIGS. 3A to 3D show a comparison of right and left arm geometries and hand locations in cartesian and joint coordinates, for the control and stroke subjects of FIGS. 2A to 2C, using the apparatus of FIG. 1. Data plotted relative to the left hand and diagonal line denote a perfect match between the actual and perceived location of the left hand or left arm geometry.
Figure 3B:
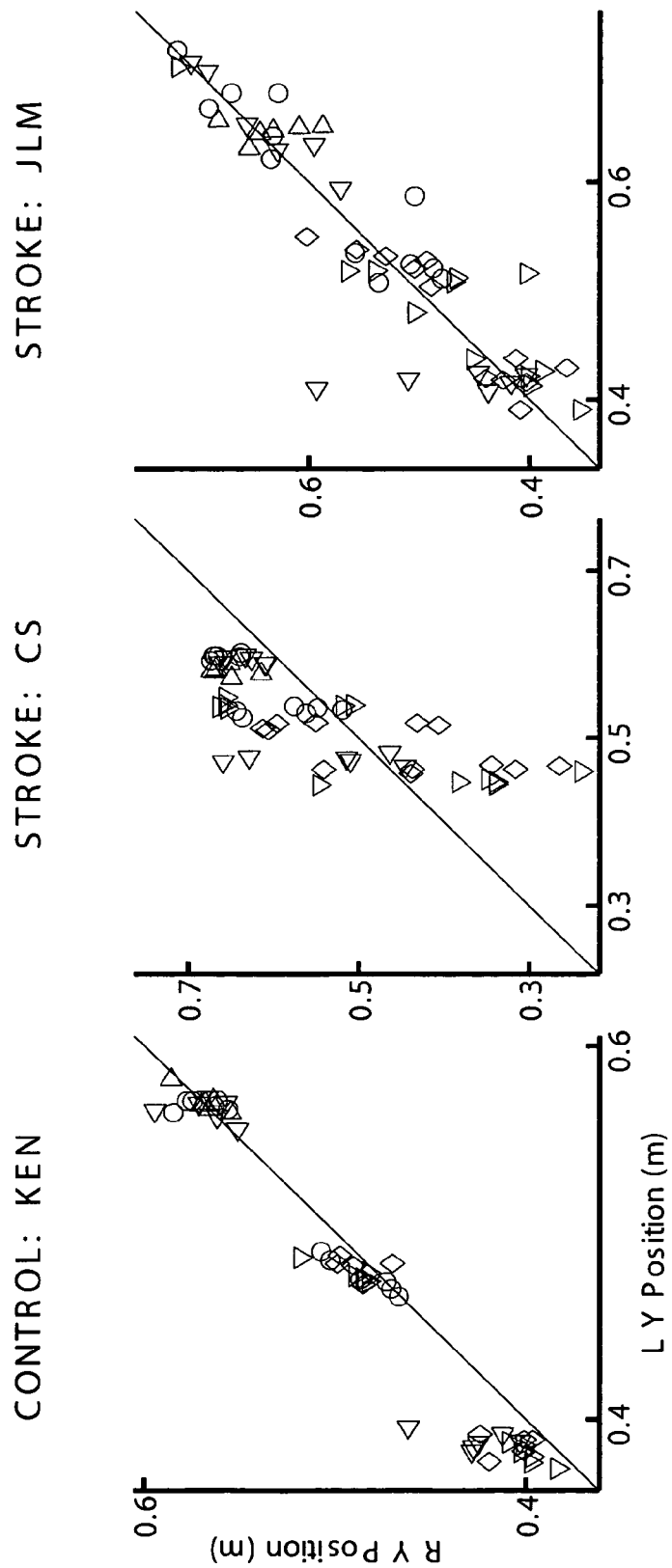
Figure 3C:
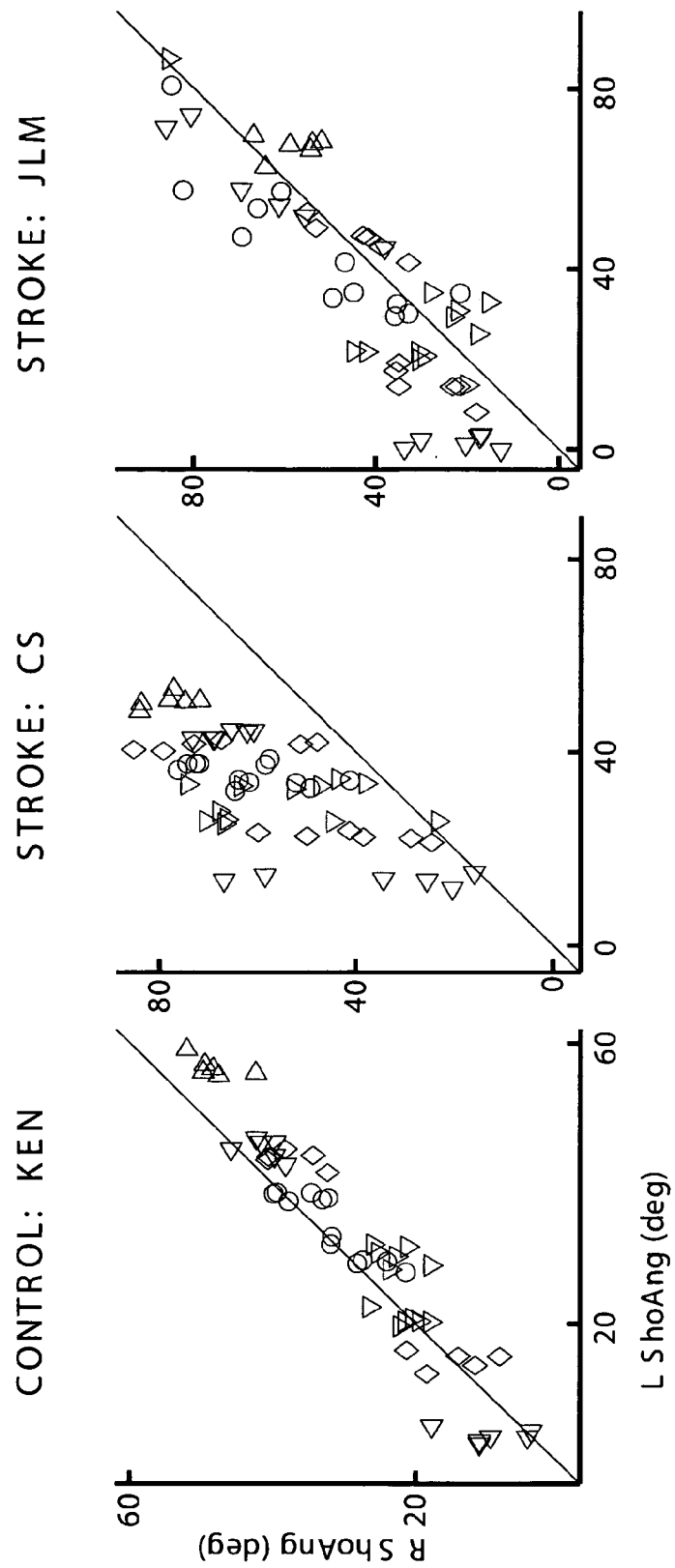

FIGS. 3A to 3D show a comparison of right and left arm geometries and hand locations in cartesian and joint coordinates, for the control and stroke subjects of FIGS. 2A to 2C. Data are plotted relative to the left hand and the diagonal line denotes a perfect match between the actual and perceived location of the left hand or left arm geometry. In FIG. 3A, the robotic linkage moved the left arm (paretic in stroke subjects) and subjects matched the geometry with the right arm. Positive X geometry is near the midline and negative is lateral. In FIG. 3B, Y hand location (away more positive) is shown. In FIGS. 3C and D, shoulder and elbow angles are shown. Several interesting features of the data are evident by comparing the ability of stroke subjects to match limb position in either cartesian or joint coordinates.

Firstly, the control subject was consistently better at maintaining hand location at the spatial target as compared to the stroke subjects. This is evident from the data for the control subject which shows small variability in hand location for the nine spatial targets.

Figure 3D:
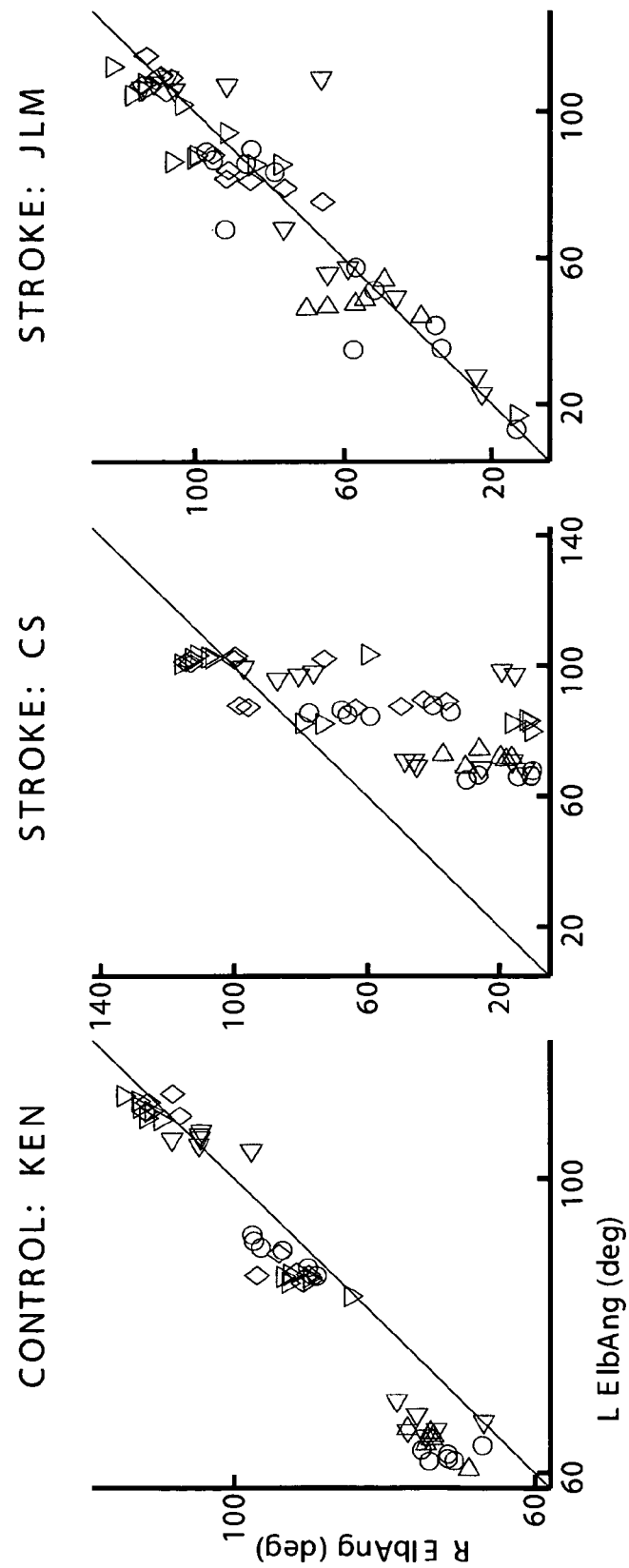

The ability of patient JLM (right posterior cerebral artery stroke (PCA) stroke) was much better for identifying the y dimension towards or away from the body (hand location in FIG. 3B, right panel, farther away being more positive) than for identifying limb position in the x direction (FIG. 3A, right panel). Note the relatively small errors for matching limb geometry near the midline, but large errors for geometries more lateral. For stroke subject CS (right middle cerebral artery (MCA) stroke), the most striking observation apart from high variability is that he showed large systematic biases in both shoulder (over-estimated angle by 20 to 30 degrees, FIG. 3C, middle panel) and elbow angles (underestimated angle from 0 to 40 degrees; FIG. 3D, middle panel). These data illustrate the utility of the apparatus for quantifying sensory deficits in stroke subjects.

It is important to note that the method of the invention can separate whether the sensory deficit is related to the joints per se, or reflects a more complex deficit related to the general spatial location of the limb relative to the body. For example, if motion at the shoulder was only examined, the two subjects JML and CS would both appear to overestimate the perceived shoulder angle. If only the elbow was examined, CS would be found to underestimate elbow angle, but patient JLM would show no systematic errors. It is only by examining both joints and using them together that a systematic spatial impairment of perceived limb position can be detected in patient JLM. Examination of at least one degree of freedom at both joints, or two degrees of freedom at the shoulder (to move the whole limb through space) differentiates these two patterns of impairment.

Figure 4:
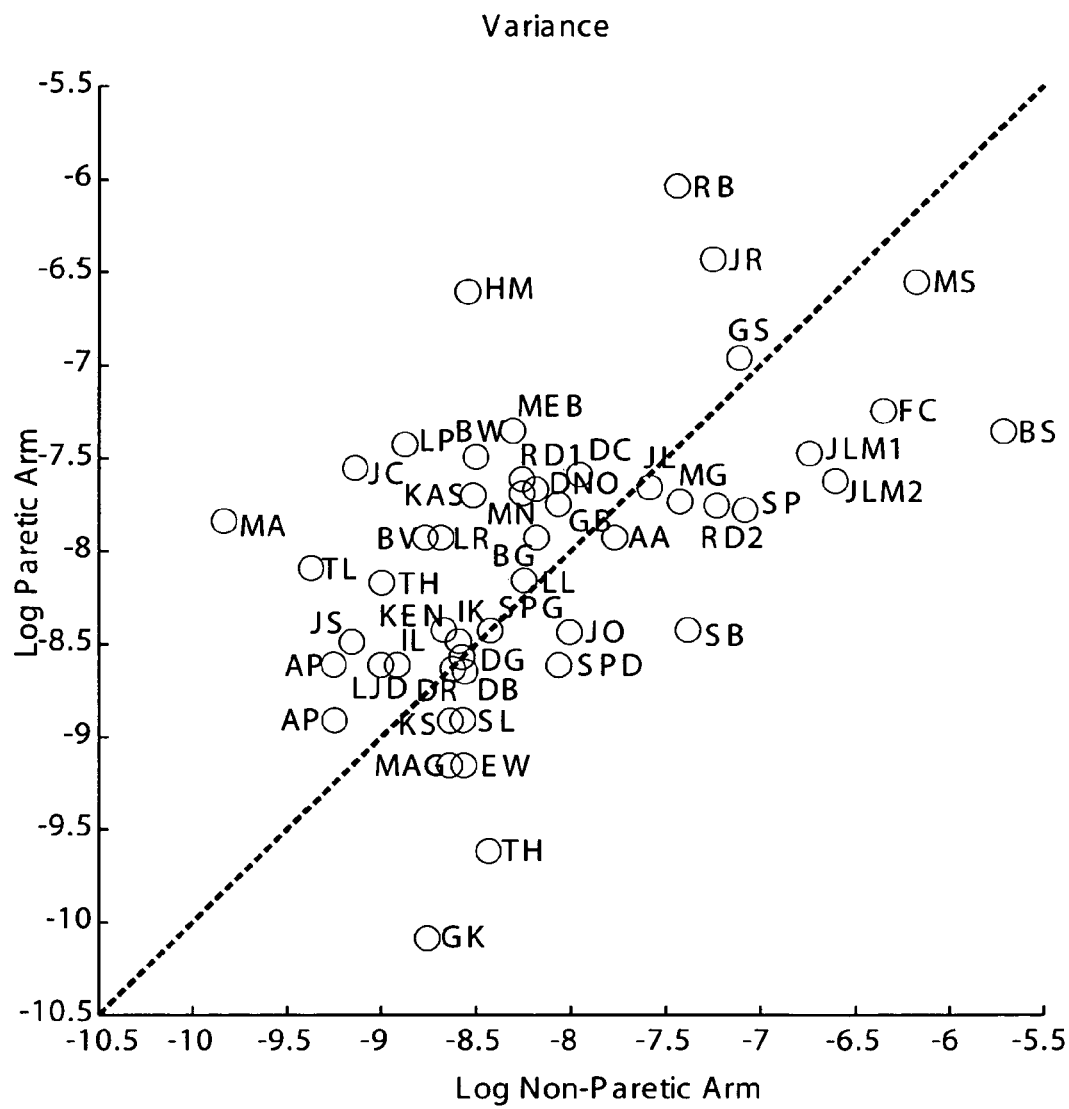
FIG. 4 is a plot showing absolute error in matching of arm geometry across nine arm geometries, for control subjects and nine stroke subjects, using the apparatus of FIG. 1. The x-axis denotes when the non-paretic limb was moved by the robotic linkage and the paretic arm was used to match, whereas the y-axis denotes when the paretic arm was moved and the non-paretic arm was used to match. Control subject data are shown such that the "non-paretic" limb is the dominant (right) arm and the "paretic limb" is the non-dominant (left) arm. Stroke subjects include HM, RB, JR, MS, FC, BS, JLM, GB and JL. Control subjects include both young (20 to 30 years old) and age-matched controls.
Figure 5:
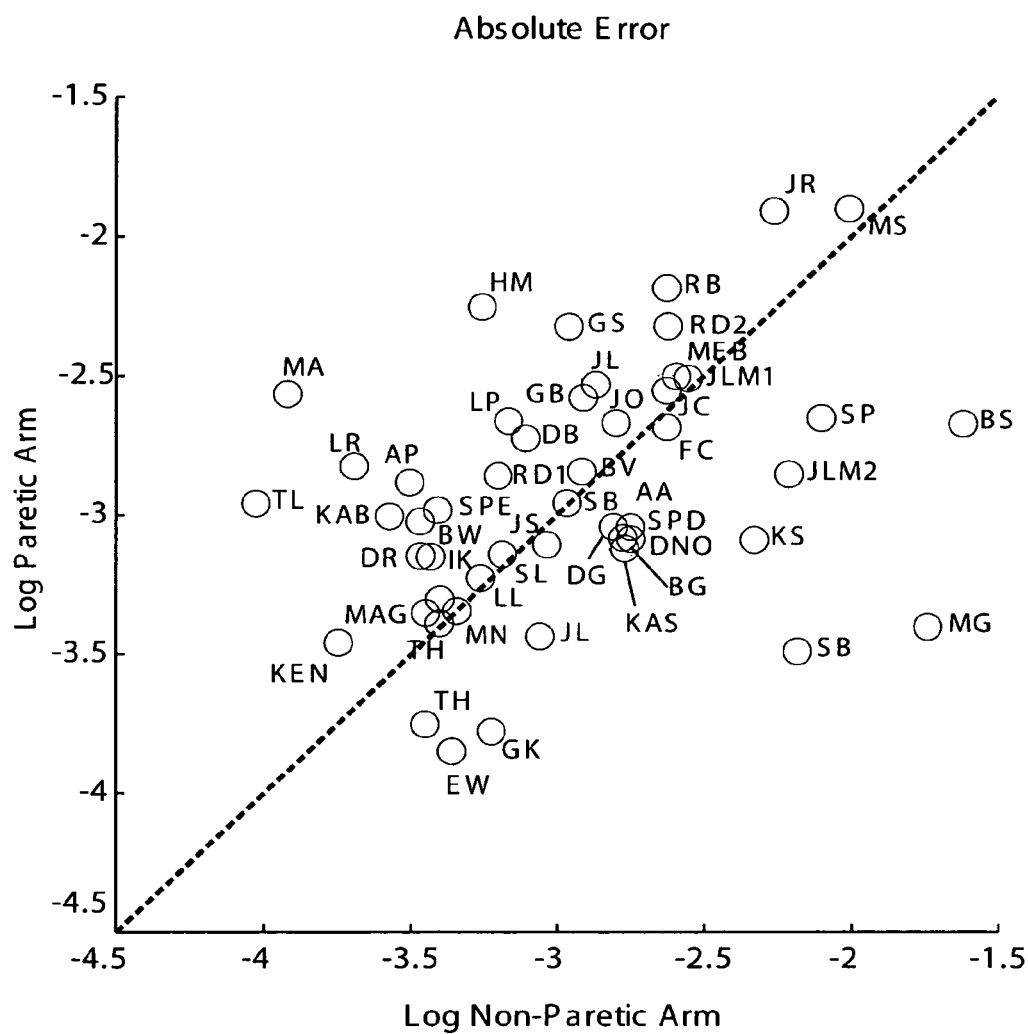
FIG. 5 is a plot showing variance in matching of limb geometry across nine arm geometries. Variability in the x direction was multiplied by the variability in the y direction, and then averaged across all nine arm geometries tested. Axes and subjects are the same as FIG. 4.

FIGS. 4 and 5 show the absolute error and variance in each subject matching the location of one hand using the other hand. While not all strokes will result in a reduction in sensory function, these figures illustrate that most stroke subjects show larger absolute errors and, in particular, greater variability in their ability to match the location of a hand with the other hand. In many cases an increase in values was observed whether the paretic or non-paretic limb was moved by the robotic linkage and in some cases, subjects tended to have greater problems with only one or the other task (e.g., compared HM versus BS). JLM was run twice in the task to demonstrate the consistency of results obtained on separate days (JLM1 versus JLM2).

Equivalents

Those skilled in the art will recognize, or be able to ascertain, equivalents to the embodiments described herein. Such equivalents are considered to be encompassed by the invention and are covered by the appended claims.

References

Alvemalm A., Furness A., Wellington L. (1996) Measurement of shoulder joint kinaesthesia. *Man Ther.* 1, 140-145.

Ariff G., et al. (2002) A real-time state predictor in motor control: study of saccadic eye movements during unseen reaching movements. *J. Neurosci.* 22, 7721-7729.

Burdet, E., Osu, R., Franklin, D. W., Milner T. E., Kawato, M. (2001) The central nervous system stabilizes unstable dynamics by learning optimal impedance. *Nature* 414, 446-449.

Carey, L., Matyas, T., Oke, L. (2002) Evaluation of impaired fingertip texture discrimination and wrist position sense in patients affected by stroke: comparison of clinical and new quantitative measures. *Journal of Hand Therapy.* 15, 71-82.

Carey, L., Oke, L., Matyas, T. (1996) Impaired limb position sense after stroke: a quantitative test for clinical use. *Archives of Physical Medicine and Rehabilitation.* 77, 1271-1278.

Elfant, I. L. (1977) Correlation between kinesthetic discrimination and manual dexterity. *American Journal of Occupational Therapy.* 31, 23-28.

Evarts, E. V, Tanji, J. (1976) Reflex and intended responses in motor cortex pyramidal tract neurons of monkey. *J Neurophysiol.* 39, 1069-80.

Haggard, P., Wolpert, D. M. (2005) Disorders of Body Scheme. *Higher-Order Motor Disorders*, Ed. Freund, Jeannerod, Hallett, Leiguarda, OUP.

Hirayama, K., Fukutake, T., Kawamura, M. (1999) Thumb localizing test for detecting a lesion in the posterior column-medial lemniscal system. *Journal of Neurological Sciences.* 167, 45-49.

Lackner, J. R. (1988). Some proprioceptive influences of the perceptual representation of body shape and orientation. *Brain*, 3, 281-97.

Lackner, J. R., DiZio, P. (1994) Rapid adaptation to coriolis force perturbations of arm trajectory. *J. Neurophysiol.* 72, 299-313.

Lackner, J. R., Dizio, P. A. (2000) Aspects of body self-calibration. *Trends in Cogn. Sci.* 4, 279-288.

Lin, J.-H., Hsueh, I-P., Sheu, C-F., Hsieh, C-L. (2004) Psychometric properties of the sensory scale of the fuglemeyer assessment in stroke patients. *Clinical Rehabilitation.* 18, 391-397.

Lincoln, N., Jackson, J., Adams, S. (1998) Reliability and revision of the Nottingham sensory assessment for stroke patients. *Physiotherapy.* 84, 358-365.

Morimoto, C. H., Amir, A., Flickner, M. (2002) Free head motion eye gaze tracking without calibration. (Interactive poster:sensory interaction) Proceedings of the CHI 2002 meeting, Apr. 20-25, 2002, pp. 586-587.

Rand, D., Gottlieb, D., Weiss, P. (2001) Recovery of patients with a combined motor and proprioception deficit during the first six weeks of post stroke rehabilitation. *Physical and Occupational Therapy in Geriatrics.* 18, 69-87.

Scheidt, R. A., Dingwell, J, B, Mussa-Ivaldi, F. A. (2001) Learning to move amid uncertainty. *J Neurophysiol.* 86, 971-85.

Scott, S. H. (2004) Optimal feedback control and the neural basis of motor control. *Nature Reviews Neuroscience* 5, 532-546.

Shadmehr, R., Mussa-Ivaldi, F. A. (1994) Rapid adaptation to coriolis force perturbations of arm trajectory. *J. Neurosci.* 14, 3208-3224.

Soechting, J. F., Lacquaniti, F. (1988) Quantitative evaluation of the electromyographic responses to multidirectional load perturbations of the human arm. *J. Neurophysiol.* 59, 1296-1313.

Teasell, R., Bayona, N., Heitzner, J. (2003) Clinical consequences of stroke. In: Teasell, R. et al., *Stroke Rehabilitation Evidence-Based Review,* 6th edition [monograph on the Internet]. London, ON: Heart & Stroke Foundation of Ontario and Canadian Stroke Network.

Van Deusen, J., Brunt, D. (1997) *Assessment in Occupational Therapy and Physical Therapy*. Philadelphia: W.B. Saunders Co.

Wang, T., Dordevic, G. S., Shadmehr, R. (2001) Learning the dynamics of reaching movements results in the modification of arm impedance and long-latency perturbation responses. *Biol. Cybern.* 85:437-448.

Wycherley, A., Helliwell, P., Bird, H. (2005) A novel device for the measurement of proprioception in the hand. *Rheumatology.* 44, 638-641.

The invention claimed is:

1. Apparatus for obtaining proprioception data for a limb or portion thereof of a subject, comprising:
    a first articulating member having first coupling means for coupling a first limb of a pair of limbs of the subject thereto, the first articulating member moveable in two or more degrees of freedom in 2- or 3-dimensional space and adapted for maintaining the limb in a desired geometry and/or at a desired location and/or for moving the limb through a desired motion in 2- or 3-dimensional space;
    a second articulating member having second coupling means for coupling a second limb of said pair of limbs of the subject thereto, the second articulating member adapted for being moved by the second limb in two or more degrees of freedom in 2- or 3-dimensional space;
    wherein the apparatus is configurable to prevent the subject from seeing the first limb or portion thereof and/or the second limb or portion thereof;
    means for obtaining angular geometry data and/or location data and/or motion data of the first limb in 2- or 3-dimensional space;
    means for obtaining angular geometry data and/or location data and/or motion data of the second limb in 2- or 3-dimensional space; and
    means for comparing said data of the first limb with said data of the second limb.

2. The apparatus of claim 1, wherein the first articulating member includes a drive system such that the first articulating member guides the first limb to a position and/or location and/or through a motion in 2- or 3-dimensional space.

3. The apparatus of claim 1, comprising:
    means for monitoring the subject's gaze direction and relating the subject's gaze direction to the angular geometry and/or location and/or motion of the first limb or portion thereof, and/or to the angular geometry and/or location and/or motion of the second limb or portion thereof, in 2- or 3-dimensional space.

4. A method for assessing proprioception in a subject, comprising:
    coupling a first limb of a pair of limbs of the subject to a first articulating member, the first articulating member moveable in two or more degrees of freedom in 2- or 3-dimensional space and adapted for maintaining the limb in a desired geometry and/or at a desired location and/or for moving the limb through a desired motion in 2- or 3-dimensional space;
    coupling a second limb of said pair of limbs of the subject to a second articulating member, the second articulating member adapted for being moved by the second limb in two or more degrees of freedom in 2- or 3-dimensional space;
    obtaining an angular geometry data and or location data and/or motion data of the first limb or portion thereof and/or of the second limb or portion thereof in 2- or 3-dimensional space, while preventing the subject from seeing the first limb or portion thereof and/or the second limb or portion thereof, the subject performing a matching task; and
    comparing said data of the first limb with said data of the second limb;
    wherein the comparison provides information about brain injury and/or a neurological disorder in the subject.

5. A method for assessing proprioception in a subject, comprising:
    coupling a first limb of a pair of limbs of the subject to a first articulating member, the first articulating member moveable in two or more degrees of freedom in 2- or 3-dimensional space and adapted for maintaining the limb in a desired geometry and/or at a desired location and/or for moving the limb through a desired motion in 2- or 3-dimensional space;
    coupling a second limb of said pair of limbs of the subject to a second articulating member, the second articulating member adapted for being moved by the second limb in two or more degrees of freedom in 2- or 3-dimensional space;
    obtaining angular geometry data and/or location data and/or motion data of the first limb or portion thereof and/or of the second limb or portion thereof in 2- or 3-dimensional space, while preventing the subject from seeing the first limb or portion thereof and/or the second limb or portion thereof, the subject performing a matching task; and
    comparing said data of the first limb with said data of the second limb;
    wherein the comparison provides information about a neural and/or muscular problem associated with impaired movement of a limb of the subject.

6. A method for assessing proprioception in a subject, comprising:
    coupling a first limb of a pair of limbs of the subject to a first articulating member, the first articulating member movable in two or more degrees of freedom in 2- or 3-dimensional space and adapted for maintaining the first limb in a desired geometry and/or at a desired location in 2- or 3- dimensional space, and/or for moving the first limb through a desired motion in 2- or 3-dimensional space;
    coupling a second limb of said pair of limbs of the subject to a second articulating member, the second articulating member adapted for being moved by the second limb in two or more degrees of freedom in 2- or 3-dimensional space;
    obtaining an angular geometry data and or location data and/or motion data of the first limb or portion thereof and/or the second limb or portion thereof in 2- or 3-dimensional space, while preventing the subject from seeing the first limb or portion thereof and/or the second limb or portion thereof, the subject performing a matching task;
    monitoring the subject's gaze direction as the subject is looking toward the perceived location of the first limb or portion thereof and/or the second limb or portion thereof; and
    relating the subject's gaze direction to the angular geometry and/or location and/or motion of the first limb or portion thereof and/or the second limb or portion thereof in 2- or 3-dimensional space;
    wherein relating the subject's gaze direction to the angular geometry and/or location and/or motion of the first limb or portion thereof and/or the second limb or portion thereof in 2- or 3-dimensional space provides information about brain injury and/or a neurological disorder in the subject.

7. A method for assessing proprioception in a subject, comprising:
- coupling a first limb of a pair of limbs of the subject to a first articulating member, the first articulating member movable in two or more degrees of freedom in 2- or 3-dimensional space and adapted for maintaining the first limb in a desired geometry and/or at a desired location in 2- or 3- dimensional space, and/or for moving the first limb through a desired motion in 2- or 3-dimensional space;
- coupling a second limb of said pair of limbs of the subject to a second articulating member, the second articulating member adapted for being moved by the second limb in two or more degrees of freedom in 2- or 3-dimensional space;
- obtaining an angular geometry data and/or location data and/or motion data of the first limb or portion thereof and/or the second limb or portion thereof in 2- or 3-dimensional space, while preventing the subject from seeing the first limb or portion thereof and/or the second limb or portion thereof, the subject performing a matching task;
- monitoring the subject's gaze direction as the subject is looking toward the perceived location of the first limb or portion thereof and/or the second limb or portion thereof; and
- relating the subject's gaze direction to the angular geometry and/or location and/or motion of the first limb or portion thereof and/or the second limb or portion thereof in 2- or 3-dimensional space;
- wherein relating the subject's gaze direction to the angular geometry and/or location and/or motion of the first limb or portion thereof and/or the second limb or portion thereof in 2- or 3-dimensional space provides information about a neural and/or muscular problem associated with impaired movement of a limb of the subject.

8. A method for assessing proprioception in a subject, comprising:
- coupling a first limb of a pair of limbs of the subject to a first articulating member, the first articulating member moveable in two or more degrees of freedom in 2- or 3-dimensional space and adapted for maintaining the limb in a desired geometry and/or at a desired location and/or for moving the limb through a desired motion in 2- or 3-dimensional space;
- coupling a second limb of said pair of limbs of the subject to a second articulating member, the second articulating member adapted for being moved by the second limb in two or more degrees of freedom in 2- or 3-dimensional space;
- obtaining angular geometry data and/or location data and/or motion data of the first limb or portion thereof and/or of the second limb or portion thereof in 2- or 3-dimensional space, while preventing the subject from seeing the first limb or portion thereof and/or the second limb or portion thereof without covering the subject's eyes, the subject performing a matching task; and
- comparing said data of the first limb with said data of the second limb;
- wherein the comparison provides information about proprioception relating to the subject's limbs.

9. A method for assessing proprioception in a subject, comprising:
- coupling a first limb of a pair of limbs of the subject to a first articulating member, the first articulating member movable in two or more degrees of freedom in 2- or 3-dimensional space and adapted for maintaining the first limb in a desired geometry and/or at a desired location in 2- or 3- dimensional space, and/or for moving the first limb through a desired motion in 2- or 3-dimensional space;
- coupling a second limb of said pair of limbs of the subject to a second articulating member, the second articulating member adapted for being moved by the second limb in two or more degrees of freedom in 2- or 3-dimensional space;
- obtaining angular geometry data and/or location data and/or motion data of the first limb or portion thereof and/or the second limb or portion thereof in 2- or 3-dimensional space, while preventing the subject from seeing the first limb or portion thereof and/or the second limb or portion thereof without covering the subject's eyes, the subject performing a matching task;
- monitoring the subject's gaze direction as the subject is looking toward the perceived location of the first limb or portion thereof and/or the second limb or portion thereof; and
- relating the subject's gaze direction to the angular geometry and/or location and/or motion of the first limb or portion thereof and/or the second limb or portion thereof in 2- or 3-dimensional space;
- wherein relating the subject's gaze direction to the angular geometry and/or location and/or motion of the first limb or portion thereof and/or the second limb or portion thereof in 2- or 3-dimensional space provides information about proprioception associated with the subject's limbs.

* * * * *

UNITED STATES PATENT AND TRADEMARK OFFICE
CERTIFICATE OF CORRECTION

PATENT NO.         : 8,277,396 B2
APPLICATION NO.    : 11/979467
DATED              : October 2, 2012
INVENTOR(S)        : Stephen H. Scott and Ian E. Brown Page 1 of 1

It is certified that error appears in the above-identified patent and that said Letters Patent is hereby corrected as shown below:

In the Claims:

Column 19, Claim 4, line 61 should read as follows:
--obtaining angular geometry data and/or location data--

Column 20, Claim 6, line 47 should read as follows:
--obtaining angular geometry data and/or location data--

Column 21, Claim 7, line 16 should read as follows:
--obtaining angular geometry data and/or location data--

Signed and Sealed this
Twenty-third Day of July, 2013

Teresa Stanek Rea
*Acting Director of the United States Patent and Trademark Office*